United States Patent [19]

Bullock

[11] Patent Number: 4,670,009

[45] Date of Patent: Jun. 2, 1987

[54] BACKFORM INSERTS FOR CATHETER

[75] Inventor: Karl D. Bullock, Irvine, Calif.

[73] Assignee: American Hospital Supply Corp., Evanston, Ill.

[21] Appl. No.: 723,912

[22] Filed: Apr. 16, 1985

[51] Int. Cl.[4] ............................................. A61M 25/00
[52] U.S. Cl. ..................................... 604/280; 604/43; 604/902
[58] Field of Search ..................... 604/43, 902, 280, 27

[56] References Cited

U.S. PATENT DOCUMENTS

| | | | |
|---|---|---|---|
| 4,270,542 | 6/1981 | Plumley | 604/43 |
| 4,385,631 | 5/1983 | Uthmann | 604/43 |
| 4,543,087 | 9/1985 | Sommercorn et al. | 604/43 |
| 4,553,957 | 11/1985 | Williams et al. | 604/43 |

Primary Examiner—Stephen C. Pellegrino
Assistant Examiner—John D. Ferros
Attorney, Agent, or Firm—Gordon L. Peterson

[57] ABSTRACT

A catheter comprising an elongated catheter body having a proximal end and at least one lumen therein opening at the proximal end, at least one extension tube, and a coupling for coupling the extension tube to the catheter body. The coupling includes an insert having a passage extending therethrough for receiving a portion of the extension tube and a main body extending over at least portions of the insert and a proximal region of the catheter body for use in retaining the extension tube, insert and catheter body together. The main body has at least one passage for use in joining the passage of the extension tube to the lumen.

18 Claims, 5 Drawing Figures

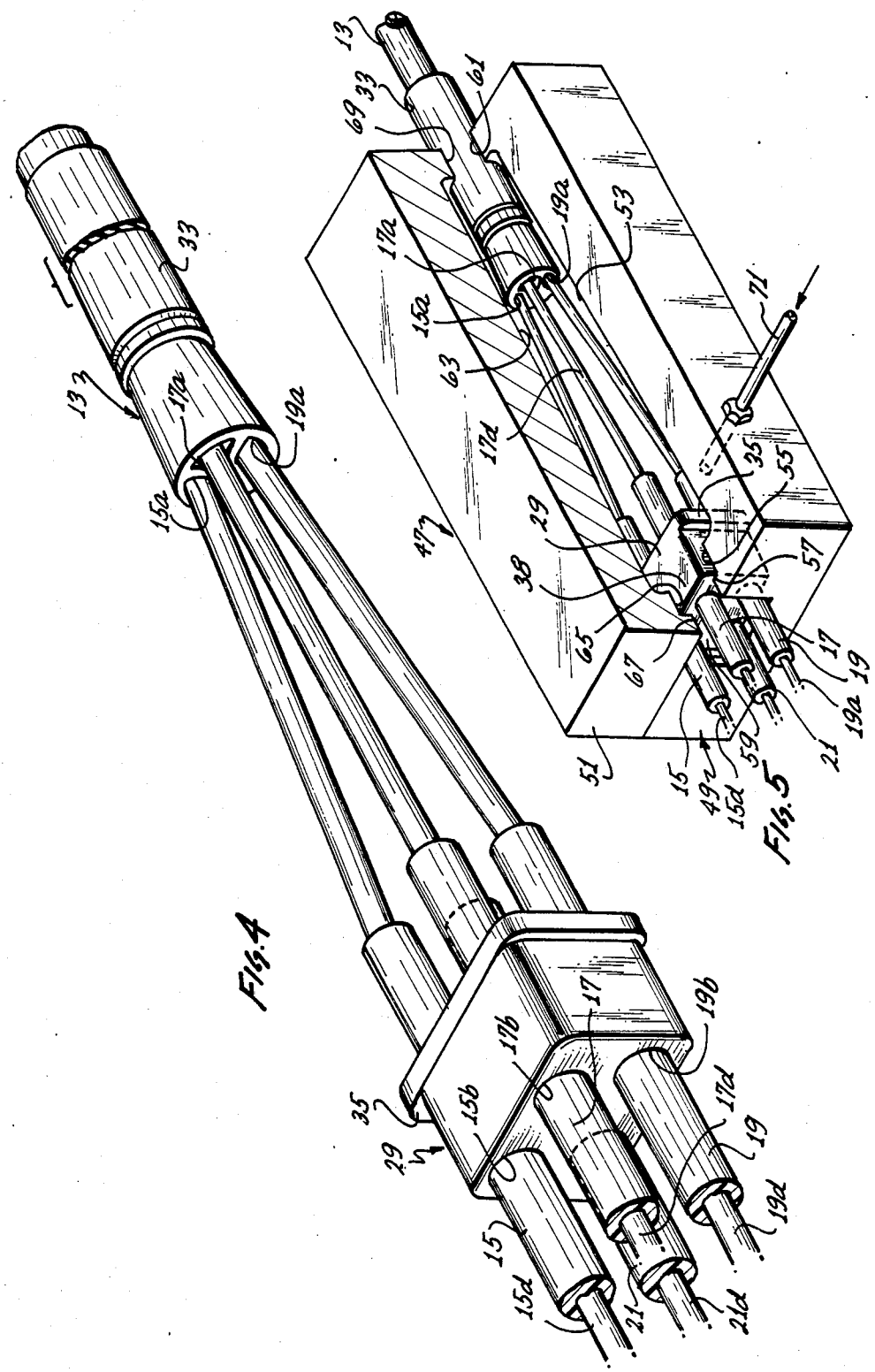

BACKFORM INSERTS FOR CATHETER

BACKGROUND OF THE INVENTION

A catheter includes an elongated catheter body adapted to be inserted, for example, into a vein or an artery for various medical purposes. The catheter body has one or more lumens, and each of the lumens is adapted to perform a different function. For example, the lumens may carry conductive leads, provide for inflation and deflation of a balloon, carry medication or other substances for infusion into the patient, sample body fluids, or be used in the measurement of blood pressure or the like. Because each lumen performs a different function, it is common practice to couple each of the lumens to different locations or connectors with extension tubes.

One common way to couple the extension tubes to the proximal end of the catheter body would be to bond the extension tubes to a plastic adapter which in turn is bonded to the catheter body. This technique is very labor intensive and requires long staging times for drying of the adhesive. In addition, the adhesive may flow into one or more of the lumens and cause a partial or complete blockage.

To eliminate the bonding, wire mandrels can be inserted through each of the extension tubes and into the associated lumen of the catheter body. A coupling body can then be injection molded around the extension tubes and a proximal portion of the catheter body to join the extension tubes to the catheter body. The mandrels are then removed to provide passages in the coupling body leading from the extension tubes to the associated lumens.

Unfortunately, this molding process is unable to accommodate the normal tolerance variations in outside diameters of the extension tubes and catheter body. Consequently, relatively large diameter extension tubes or catheter bodies tend to melt in the mold, and the relatively small diameter extension tubes and catheter bodies permit the plastic being injection molded to "flash" out of the mold along the outside of the extension tubes and/or catheter body. In addition, contacting the hot plastic used for injection molding directly onto the catheter body and extension tubes tends to cause kinking or lumen collapse during normal use of the catheter. Finally, this technique required a separate mold for each catheter having a different number of lumens.

SUMMARY OF THE INVENTION

This invention provides an extension tube to catheter body coupling and a method which overcome these problems and achieve various other advantages. The coupling includes an insert having a passage extending therethrough for receiving a portion of the extension tube. A main body receives at least portions of the insert and a proximal region of the catheter body for use in retaining the extension tube, insert and catheter body together. The main body has a passage for use in joining the passage of the extension tube to the associated lumen so that the extension tube communicates with the lumen.

The method and apparatus features of this invention are applicable to both single and multiple-lumen catheter bodies. Generally, the number of extension tubes and passages in the main body should correspond with the number of lumens in the catheter body.

The insert provides a number of significant advantages. For example, the passages through the insert which receive the extension tubes can be large enough to accommodate the production tolerances of the extension tubes. The main body is molded, and during molding, plastic cannot flash through any gap between the passage wall and the associated extension tube because any plastic entering such gap cools and hardens before it can reach the exterior of the insert. Accordingly, any plastic flow of this type simply increases the strength of the connection between the extension tube and the insert. The insert also shields significant lengths of the extension tubes from being contacted directly by the hot plastic which is to form the main body of the coupling.

With this invention, the mold for the main body preferably closes off around the insert. Accordingly, the mold need not be sized to accommodate any particular number, or outside diameter, of extension tubes. With this construction, a single mold can be used for catheters having different numbers of lumens, provided that the exterior size and configuration of the inserts for each of these catheter bodies are the same. The insert is preferably not totally rigid so that the insert can be compressively loaded and deformed slightly by the mold when the mold is being closed off at the insert. This assures that no plastic will flash through the mold-insert interface and allows the insert to be separately molded with looser tolerances. Because the mold preferably closes off around the insert, the insert extends proximally of the main body following the molding operation. Another important function of the insert is to serve as a fixture to at least assist in retaining the extension tubes in position in the mold.

Another feature of this invention is that the coupling includes a sleeve which receives a portion of the catheter body and is at least partially received by the main body of the coupling. The sleeve also performs several important functions. For example, during molding, the mold is closed off around the sleeve in a manner similar to that described above for the insert. Consequently, by compressively loading the sleeve with the mold, the likelihood of plastic flashing through the mold-sleeve interface is greatly reduced. By extending the sleeve into the mold so that at least a portion of it is received by the main body, the portion of the catheter body which is received by the main body is shielded, or partly shielded, from direct contact with the hot plastic which is to form the main body. By extending the sleeve distally of the main body, the sleeve provides a transition between the relatively stiff main body and the relatively flexible catheter body to thereby provide strain relief.

To provide for a strong attachment, the catheter body preferably extends proximally of the sleeve, and the extension tubes extend distally of the insert. Consequently, the plastic of the main body can directly contact the sleeve, the catheter body, the extension tubes and the insert to strongly join all of these members together.

Generally, the method of this invention can be carried out by inserting one or more of the extension tubes through corresponding passages of an insert so that portions of the extension tubes are on opposite sides of the insert. A main body is then molded over at least portions of the insert and a proximal region of the connector body to retain the extension tubes, the insert, and connector body together and to form passages in the main body for at least assisting in providing communication between the extension tubes and the lumens. If the sleeve is used, a portion of the main body is molded over at least a portion of the sleeve.

In a broader sense, each of the insert and sleeve form an adapter which adapts a member (the extension tube or catheter body) to be molded into the main body. Although this invention contemplates the use of both the insert and the sleeve, each of these may be used without the other, if desired.

To form the passages extending between the extension tubes and the lumens, mandrels are inserted through the extension tubes and into the associated lumens before the molding is carried out. The mandrels are withdrawn following the curing of the plastic of the main body.

The invention, together with additional features and advantages thereof, may best be understood by reference to the following description taken in connection with the accompanying illustrative drawing.

BRIEF DESCRIPTION OF THE DRAWING

FIG. 4 is a fragmentary, isometric view illustrating an early step in one embodiment of the method of this invention.

FIG. 5 is a fragmentary, isometric view showing one section of the mold being broken away in section and illustrating one way in which the molding step can be carried out.

DESCRIPTION OF THE PREFERRED EMBODIMENT

Figure 1:
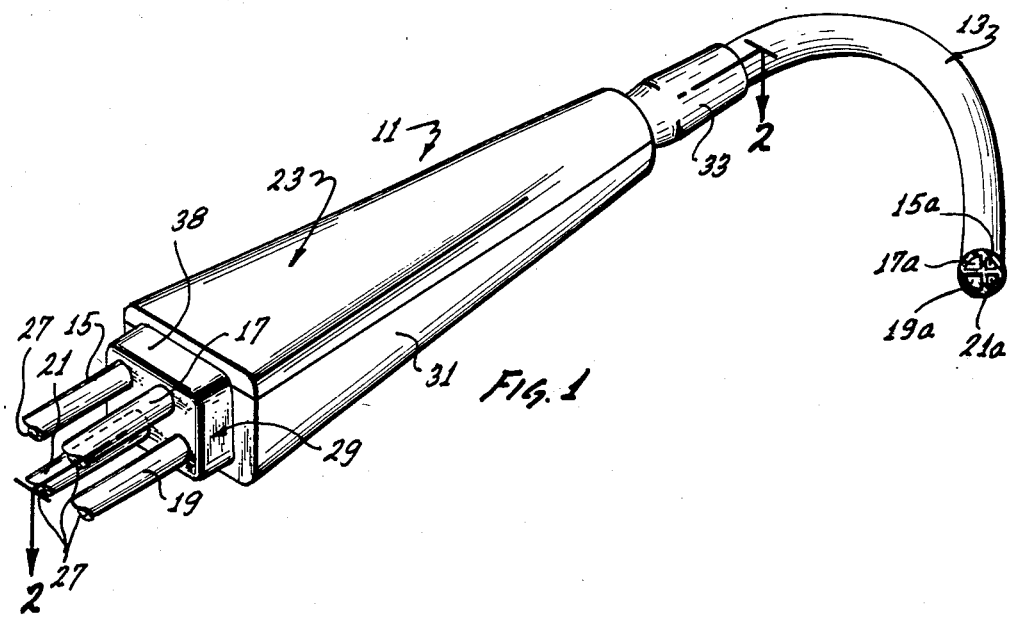
FIG. 1 is a fragmentary, isometric view of a catheter constructed in accordance with the teachings of this invention, with only a proximal portion of the catheter body being illustrated.
Figure 2:
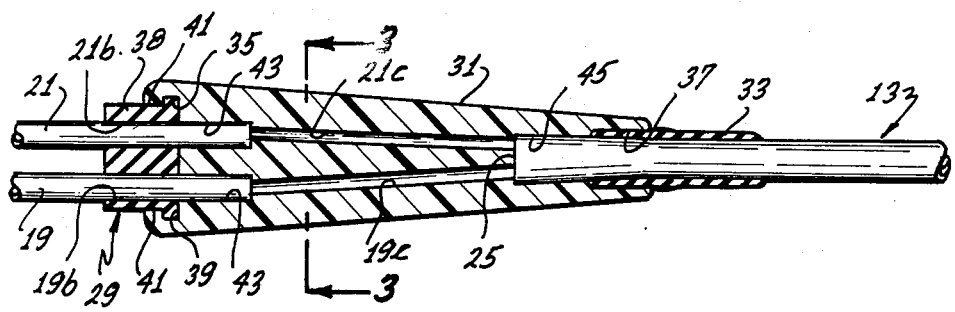
FIG. 2 is a fragmentary, sectional view taken generally along line 2—2 of FIG. 1.
Figure 3:
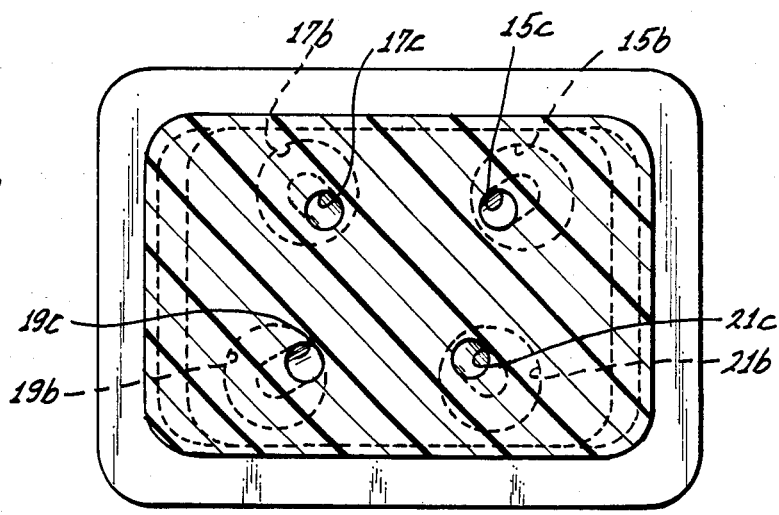
FIG. 3 is an enlarged sectional view taken generally along line 3—3 of FIG. 2.

FIGS. 1–3 show a catheter 11 which generally comprises an elongated catheter body 13, four extension tubes 15, 17, 19 and 21, and a coupling 23 for coupling the extension tubes to the catheter body. The catheter body 13 may be of conventional construction and comprise one or more lumens. In the embodiment illustrated, the catheter body 13 has four lumens 15a, 17a, 19a and 21a corresponding, respectively, to the extension tubes 15, 17, 19 and 21. Although the lumens may perform various different functions, in the embodiment illustrated, the lumens 15a, 17a, 19a, and 21a are used for pressure sensing, balloon inflation and deflation, thermistor lead wires and infusion. In this regard, the catheter 11 may include various other elements, such as a balloon, thermistor, infusion port and sensing port, as well as various other members, which are not illustrated because they form no portion of the present invention.

The catheter body 13 is flexible, constructed of a biocompatible plastic material, such as PVC, and sized to be received within a vein or an artery. The catheter body 13 has a proximal end 25 (FIG. 2).

The extension tubes 15, 17, 19, and 21 may be identical, and each of them has an axial passage 27 extending completely through it. Each of the extension tubes 15, 17, 19 and 21 is elongated and flexible and may be constructed, for example, of a suitable plastic material, such as PVC. The extension tubes 15, 17, 19 and 21 lead to separate connectors (not shown) which will enable each of the associated lumens 15a, 17a, 19a and 21a to carry out its intended function.

The coupling 23 includes an insert 29, a main body 31 and a sleeve 33. Like the extension tubes and catheter body 13, the insert 29 and the sleeve 33 are each constructed of a suitable plastic material, such as PVC, which will enable them to be bonded to the plastic of the main body 31 during the insert molding process described hereinbelow with reference to FIGS. 4 and 5. For example, the main body 31 may be constructed of Hytrel which is obtainable from Dupont.

The insert 29 is relatively rigid, but at least somewhat deformable under compressive loads. The insert 29 has four parallel passages 15b, 17b, 19b and 21b for receiving the extension tubes 15, 17, 19 and 21, respectively. The number of the passages through the insert 9 corresponds to the number of the extension tubes. The insert 29 is generally in the form of a rectangular solid as shown in FIGS. 1 and 4 and has opposite flanges 35 at its distal end.

The main body 31 receives distal portions of the insert 29 and the extension tubes and proximal portions of the catheter body 13 and sleeve 33. The main body 31 is relatively rigid and provides passages 15c, 17c, 19c and 21c extending from the lumens 15a, 17a, 19a, and 21a to the associated passages 15b, 17b, 19b and 21b. As shown in FIG. 2, the passages through the main body 31 converge as they extend toward the catheter body 13. Although various external configurations are possible, in this embodiment, the main body 31 tapers as it extends toward the catheter body 13.

The sleeve 33 receives a portion of the catheter body 13 and is partially received by the main body 31. The catheter body 13 extends proximally of the sleeve 33 so that a portion of the catheter body is in direct contact with the main body 31. The sleeve 33 is a thin-wall, flexible tube which is in intimate contact with the outer surface of the catheter body 13 and an inner surface 37 of the main body 31.

A proximal portion 38 of the insert 29 extends proximally of the main body 31, and the main body has a cavity 39 for receiving a distal portion of the insert. The main body 31 also has opposite flanges 41 for interlocking with the flanges 35 to strongly retain the insert to the main body.

The extension tubes 15, 17, 19 and 21 extend completely through their associated passages in the insert 29 and project equal distances beyond the distal end of the insert into correspondingly shaped recesses 43 in the main body where they meet the associated passages 15c, 17c, 19c and 21c of the main body. These latter passages in turn extend all the way to the associated lumens 15a, 17a, 19a and 21a of the catheter body 13. In this regard, the catheter body 13 is received in a correspondingly shaped recess 45 of the main body 31. With this construction, the main body 31 contacts and joins together the insert 29, the tubes 15, 17, 19 and 21, the catheter body 13 and the sleeve 33. A region of the sleeve 33 extends distally of the main body 31 to provide strain relief.

FIGS. 4 and 5 show a preferred method of making the coupling 23. First, the extension tubes 15, 17, 19 and 21 are loaded a predetermined distance into the corresponding passages 15b, 17b, 19b and 21b of the insert 29 to axially position the tubes. Portions of the extension tubes are on opposite sides of the insert as shown in FIG. 4. The extension tubes are frictionally retained in the insert 29. At any time before, during or after the loading of the extension tubes into the insert 29, the sleeve 33 is installed at a predetermined axial location on the proximal end of the catheter body 13. In the production of the catheter body 13, the proximal region of the catheter body 13 is expanded radially outwardly. The installation of the sleeve 33 on the catheter body 13 includes inserting the distal end of the catheter body into the sleeve and advancing the sleeve proximally over the radially expanded region to the desired location. The sleeve tightly grips the expanded region and is frictionally retained at the desired proximal location on the catheter body. The sleeve 33 accommodates catheter body outside diameter variances due to production tolerances. Next, tapered mandrels 15d, 17d, 19d and 21d are inserted through the tubes 15, 17, 19 and 21, respectively, and into the associated lumens 15a, 17a, 19a, and 21a (FIG. 4) where they are frictionally retained by the catheter body 13.

FIG. 5 shows somewhat schematically a mold 47 which comprises mold sections 49 and 51 which can be relatively moved toward each other to a closed position shown in FIG. 5 and relatively moved away from each other to an open position. With the mold 47 in the open position, the entire assembly of FIG. 5 is inserted into a cavity 53 of the mold section 49. The mold section 49 has a recess 55 which forms a portion of the mold cavity 53 and which receives a major portion of the proximal portion 38 of the insert 29. The mold section 49 has a shoulder 57 at the left end (as viewed in FIG. 5) against which the proximal face of the insert 29 can be seated. This positively locates and retains the insert 29. The insert 29 then serves as a fixture to locate and retain in position in the mold 47 the extension tubes, mandrels, sleeve 33 and catheter body 13, all of which were axially positioned relative to the insert as described above with respect to FIG. 4. The mold section 49 has an opening 59 leading to the recess 55 through which the extension tubes 15, 17, 19 and 21 and the associated mandrels project.

The other end of the mold section 49 has an opening 61 which snugly receives a lower portion of the sleeve 33. The sleeve 33 and the catheter body 13 extend through the opening 61 into the mold cavity 53.

The mold section 51 has a cavity 63 which cooperates with the cavity 53 to define the desired exterior configuration of the main body 31. In addition, the mold section 51 has a recess 65 and a shoulder 67 for cooperating with the recess 55 and the shoulder 57 to receive and locate the insert 29. The opposite end of the mold section 51 has an opening 69 which cooperates with the opening 61 to snugly receive and compressively load the sleeve 33. The surfaces defining the recesses 55 and 65 snugly receive and compressively load the insert 29 so that both the insert and sleeve are deformed somewhat into tight conformity with their associated recesses. Thus, the recesses 55 and 65 close off the mold around the insert 29, and the openings 59 and 69 close off the recess around the sleeve 33.

With the mold 47 in the closed position shown in FIG. 5, hot plastic is injected through an inlet 71 into the mold cavities 53 and 63 to form the main body 31 which tightly retains the extension tubes, the insert 29, the catheter body 13 and the sleeve 33 together. The plastic flows around the mandrels 15d, 17d, 19d and 21d so that the mandrels form the passages 15c, 17c, 19c and 21c, respectively. After the plastic of the main body 31 cures, the mold sections 49 and 51 are relatively moved away from each other to an open position, and the catheter 11 is moved from the mold section 49. The mandrels 15d, 17d, 19d and 21d can then be removed by rotating them relative to the catheter 11 and then axially withdrawing them.

Because the mold 47 is closed off around the insert 29, the variance in diameters of the extension tubes as a result of tolerances makes no difference to the molding operation. In addition, the same mold 47 may be used for any number of extension tubes, provided the insert used with such molding operation conforms in exterior configuration to the insert 29. Because the mold 47 compressively loads and deforms the insert 29 and the sleeve 33, there is virtually no opportunity for plastic from the mold cavities 53 and 63 to flow out of the mold. Also, any flowable plastic entering the interface between the extension tubes and the associated passages in the insert 29 would harden before reaching the proximal end of the insert.

Although an exemplary embodiment of the invention has been shown and described, many changes, modifications and substitutions may be made by one having ordinary skill in the art without necessarily departing from the spirit and scope of this invention.

I claim:

1. A catheter comprising:
   an elongated catheter body having a proximal end and at least one lumen therein opening at said proximal end;
   at least one extension tube having a passage therein;
   means for coupling the extension tube to the catheter body;
   said coupling means including an insert means having a passage means extending therethrough for receiving a portion of the extension tube and a main body receiving at least portions of the insert means, a portion of the extension tube and a proximal region of the catheter body for use in retaining the extension tube, the insert means, and the catheter body together; and
   said main body having at least one passage therein for use in joining the passage of the extension tube to the lumen whereby the extension tube communicates with the lumen of the catheter body.

2. A catheter as defined in claim 1 wherein a distal portion of said extension tube extends through said passage of the insert means and is joined to said main body.

3. A catheter as defined in claim 1 wherein a proximal portion of said insert means extends proximally of the main body.

4. A catheter as defined in claim 1 wherein said insert means is spaced from the proximal end of the catheter body.

5. A catheter as defined in claim 1 including a shoulder on said insert means, said shoulder being within said main body.

6. A catheter as defined in claim 1 wherein said main body includes plastic material which is molded over said portions of the insert means and said proximal region of the catheter body.

7. A catheter as defined in claim 6 wherein a distal portion of said extension tube extends through said passage means and is joined to said main body, a proximal portion of said insert means extends proximally of the main body, and said insert means is spaced from the proximal end of the catheter body.

8. A catheter as defined in claim 1 wherein said coupling means includes a sleeve receiving a portion of the catheter body and being at least partially received by said main body.

9. A catheter as defined in claim 8 wherein said sleeve extends distally of said main body.

10. A catheter as defined in claim 9 wherein a distal portion of said extension tube extends through said passage means and is joined to said main body, a proximal portion of said insert means extends proximally of the main body, and said insert means is spaced from the proximal end of the catheter body.

11. A catheter as defined in claim 8 wherein said catheter body extends proximally of said sleeve.

12. A catheter as defined in claim 1 wherein said catheter includes a plurality of said extension tubes, said catheter body includes a corresponding number of said lumens and said main body and insert means each have a number of said passages means therein corresponding to said plurality of extension tubes, said extension tubes are received in said passages of said insert means, respectively, and said passages means in said main body join the extension tubes to associated lumens.

13. A catheter as defined in claim 1 wherein said catheter body is flexible and sized to be received within a vein or artery.

14. A catheter as defined in claim 1 wherein said insert means is at least somewhat compressively deformable.

15. A catheter comprising:
an elongated catheter body having a proximal end and at least one lumen opening at said proximal end;
at least one extension tube having a passage therein;
means for coupling the extension tube to the catheter body;
said coupling means including an adapter having a passage means extending therethrough for receiving a portion of one of the extension tube and the catheter body and a main body receiving at least portions of the adapter, the extension tube and the catheter body for use in retaining the extension tube, the adapter, and the catheter body together; and
said main body having at least one passage therein for use in joining the passage of the extension tube to the lumen whereby the extension tube communicates with the lumen of the catheter body.

16. A catheter as defined in claim 15 wherein said adapter receives a portion of the catheter body.

17. A catheter as defined in claim 15 wherein said adapter receives a portion of the extension tube.

18. A catheter as defined in claim 15 wherein said adapter includes a flexible sleeve receiving a portion of the catheter body and at least partially received in the main body.

* * * * *

UNITED STATES PATENT OFFICE
CERTIFICATE OF CORRECTION

Patent No. 4,670,009          Dated   June 2, 1987

Inventor(s)  Karl D. Bullock

It is certified that error appears in the above-identified patent and that said Letters Patent are hereby corrected as shown below:

Column 4, line 18 change "insert 9" to -- insert 29 --.

Column 6, line 48 change "of the insert means" to -- means of the insert means --.

Column 6, line 65 change "means and is" to -- means of the insert means and is --.

Column 7, line 10 after "passage means" insert -- of the insert means --.

Column 7, line 25 change "said passages of said insert means" to -- said passages means of said insert means --.

Signed and Sealed this

Fifteenth Day of December, 1987

*Attest:*

DONALD J. QUIGG

*Attesting Officer*   *Commissioner of Patents and Trademarks*